United States Patent

Kato et al.

Patent Number: 5,286,737
Date of Patent: Feb. 15, 1994

[54] METHOD FOR INHIBITING AROMATASE

[75] Inventors: Akira Kato; Junko Miyagawa, both of Tokyo; Yuko Ikeda, Chiba; Koichi Niimura, Saitama, all of Japan

[73] Assignee: Kureha Kagaku Kogyo Kabushiki Kaisha, Japan

[21] Appl. No.: 945,178

[22] Filed: Sep. 16, 1992

[30] Foreign Application Priority Data

May 21, 1992 [JP] Japan .................. 4-155782

[51] Int. Cl.$^5$ .................. A61K 31/41; A61K 31/415
[52] U.S. Cl. .................. 514/383; 514/399
[58] Field of Search .................. 514/383, 399

[56] References Cited

FOREIGN PATENT DOCUMENTS 2180236A 3/1987 United Kingdom .

Primary Examiner—Jerome D. Goldberg
Attorney, Agent, or Firm—Parkhurst, Wendel & Rossi

[57] ABSTRACT

This invention provides a method of inhibiting aromatase and treating of estrogen-dependent diseases in a patient by administering azole derivatives as nonsteroidal inhibitors. The azole derivative has the formula

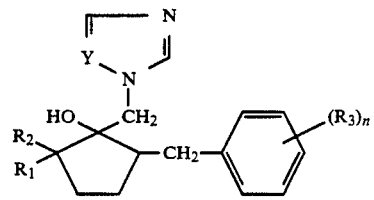

where $R_1$ a is hydrogen or a ($C_1$-$C_5$) alkyl; $R_2$ is a hydrogen or a ($C_1$-$C_5$) alkyl; $R_3$ is any of a halogen, a ($C_1$-$C_5$)alkyl, a haloalkyl, a phenyl, a cyano, or nitro; n is 0 to 5; and Y is a nitrogen atom or CH.

4 Claims, No Drawings

METHOD FOR INHIBITING AROMATASE

BACKGROUND OF THE INVENTION

1. Field of the Invention

The present invention relates to a method for inhibiting aromatase in a patient by administering certain azole derivative compounds functioning as nonsteroidal inhibitors to the patient.

2. Description of the Related Art

It is known that androgenic steroids can be converted to estrogens. In the biosynthetic pathway for estrogen formation from an androgenic steroid, aromatization, an essential step, is catalyzed by a small amount of an aromatase enzyme.

It is generally believed that, if the aromatase enzyme could be effectively inhibited, one could obtain a useful treatment for estrogen-dependent diseases. See Cancer Research, Vol. 42, Suppl. 8, 3261s (1982).

4-Hydroxyandrostenedione is well-known as an aromatase inhibitor (Biochem. Pharmacol 31(5), 701–705 (1982)). However, the potency, selectivity, and side-effect properties of 4-hydroxyandrostenedione are such that the compound is not readily useful in treating patients.

The present inventors have studied compounds useful for inhibiting the aromatase enzyme in a patient and discovered that azole derivatives of formula (I) herein have an inhibitory effect on the aromatase enzyme.

SUMMARY OF THE INVENTION

The present invention provides a method for inhibiting aromatase in a patient by administering to the patient an effective amount of an azole derivative (or a pharmaceutically acceptable salt thereof) of formula (I)

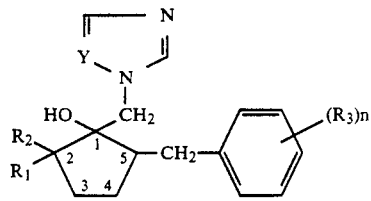

wherein:
- $R_1$ represents a hydrogen atom or a $(C_1-C_5)$ alkyl group;
- $R_2$ represents a hydrogen atom or a $(C_1-C_5)$ alkyl group;
- $R_3$ represents a halogen atom, a $(C_1-C_5)$ alkyl group, a haloalkyl group, a phenyl group, a cyano group, or a nitro group, $R_3$ being the same or different from each other;
- n represents an integer of 0 to 5; and
- Y represents a nitrogen atom or CH.

By virtue of their ability to inhibit aromatase, the azole derivatives of formula (I) are useful in the treatment and prevention of estrogen-dependent diseases, for example, breast cancer in a patient, especially estrogen-dependent breast cancer.

DESCRIPTION OF THE PREFERRED EMBODIMENTS

The compounds used in the present invention are represented by formula (I) above. In a preferred embodiment R is a hydrogen atom and $R_2$ is a $(C_1-C_5)$ alkyl, especially when $R_1$ is a $(C_2-C_5)$ alkyl group.

Since the compounds of formula (I) have an azolylmethyl group at the 1-position, a hydrogen atom or a $(C_1-C_5)$ alkyl group at the 2-position, and a substituted benzyl group at the 5-position, respectively, of a cyclopentane ring, the compounds have geometric isomers and optical isomers. The compounds used in the present invention include all of these respective isomers and mixtures of any number of isomers in any ratio. Accordingly, aromatase inhibitors used in the present invention may contain a single isomer or a mixture of these isomers as an effective ingredient. The compounds of formula (I) can be synthesized in accordance with the methods described in Japanese Application Laid-open (KOKAI) 64-79117 (1989) (See European Patent Publication 0294222-A2 for an English counterpart) and Japanese Application Laid-Open (KOKAI) 1-93574 (1989) (See European Patent Publication 0267778-A2 for an English counterpart.) The azole derivative is produced through a process comprising the steps of:

a)(i) reacting an alkyl ester of 2-oxocyclopentanecarboxylic acid with a substituted benzyl halide or reacting the thus obtained alkyl ester of 1-(substituted benzyl)-2-oxocyclopentanecarboxylic acid with a $(C_1-C_5)$alkyl halide, (ii) reacting an alkyl ester of 3-$(C_1-C_5)$alkyl-2-oxocyclopentanecarboxylic acid with a substituted benzyl halide, or (iii) reacting 1-(substituted benzyl) -3-$C_1-C_5$ alkyl) -2-oxocyclopentanecarboxy acid with a $(C_1-C_5)$alkyl halide, thereby obtaining an ester derivative of cyclopentanecarboxylic acid represented by the formula (V):

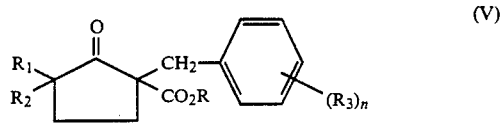

wherein $R_1$ and $R_2$ represent either a hydrogen atom or a $(C_1-C_5)$alkyl group; $R_3$ represents a halogen atom, a $(C_1-C_5)$alkyl group, a haloalkyl group, a phenyl group, a cyano group, or a nitro group, $R_3$ being the same or different from each other; R is a $(C_1-C_5)$ alkyl group; and n represents an integer of from 0 to 5, b) subjecting the thus obtained ester derivative of cyclopentanecarboxylic acid to hydrolytic decarboxylation, thereby obtaining a cyclopentanone derivative represented by the formula (IV):

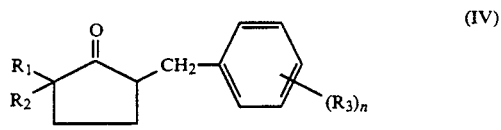

wherein $R_1$, $R_2$, $R_3$, and n respectively represent the same defined as above, c) subjecting the thus obtained cyclopentanone derivative to an oxirane reaction while using sulfonium ylide or sulfoxonium ylide to epoxidation, thereby converting the cyclopentanone derivative into an oxirane derivative represented by the formula (II):

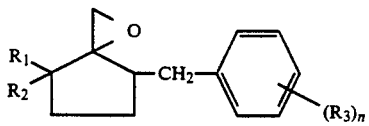

(II)

wherein $R_1$, $R_2$, $R_3$, and n respectively represent the same defined as above, and then d) reacting the thus obtained oxirane derivative with a 1,2,4-triazole or an imidazole alkaline metal salts represented by the formula (III):

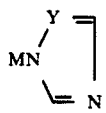

(III)

wherein M represents a hydrogen atom or an alkali metal atom and Y represents a nitrogen atom or a CH, thereby obtaining the azole derivative represented by the formula (I):

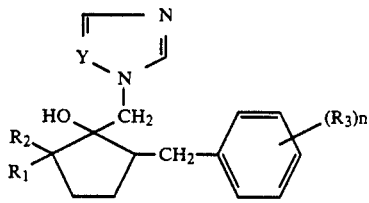

(I)

wherein $R_1$ and $R_2$ represent either a hydrogen atom or a ($C_1$–$C_5$)alkyl group; $R_3$ represents a halogen atom, a ($C_1$–$C_5$)alkyl group, a haloalkyl group, a phenyl group, a cyano group, or a nitro group, $R_3$ being the same or different; n represents an integer of from 0 to 5; and Y represents a nitrogen atom or CH.

As the diluent used in reactions in the process of producing the azole derivative represented by formula (I), hydrocarbons such as benzene, toluene, xylene, etc.; halogenohydrocarbons such as methylene chloride, chloroform, carbon tetrachloride, etc.; alcohols such as methanol, ethanol, etc.; ethers such as diethyl ether, diisopropyl ether, tetrahydrofuran, dioxane, etc. and as the others, acetonitrile, acetone, dimethylformamide, dimethylsulfoxide, etc. may be exemplified.

Still more, in the process for producing the azole derivative, the reaction is carried out in the presence of a base or an acid in addition to the above-mentioned diluent. As the base used herein, alkali metal carbonates such as sodium carbonate, potassium carbonate, etc., alkali metal hydroxides such as sodium hydroxide, potassium hydroxide, etc.; alkali metal alcoholates such as sodium methoxide, sodium ethoxide, potassium t-butoxide, etc.; alkali metal hydrides such as sodium hydride, potassium hydride, etc.; alkyl compounds of an alkali metal such as n-butyl lithium, etc. and as the other, triethylamine, pyridine may be exemplified.

As the acid, inorganic acids such as hydrochloric acid, hydrobromic acid, hydroiodic acid, sulfuric acid, etc. and organic acids such as formic acid, acetic acid, butyric acid, p-toluenesulfonic acid, etc. may be exemplified.

In order to enhance the process for production of the azole derivative, for instance, in the case of obtaining the ester derivative of cyclopentanecarboxylic acid represented by formula (V), it is preferable to react a halogenated alkyl or a substituted benzyl halide with a compound represented by the formula:

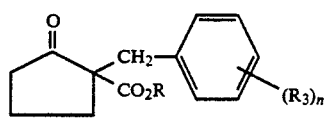

or the formula:

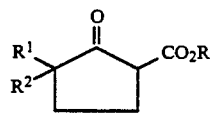

which has been dissolved in the diluent, in the presence of the base as occasion demands. The reaction temperature may be selected optionally in the range of from the solidifying temperature of the diluent as the solvent to the boiling point thereof, preferably from 0° to 100° C.

The derivative represented by formula (IV) can be obtained by subjecting the ester derivative of cyclopentanecarboxylic acid represented by formula (V) to decarboxylation at a temperature of from 80° to 150° C. with the inorganic acid or organic acid for from 2 to 24 hours, preferably with stirring under inert atomosphere.

In order to obtain the azole derivative represented by formula (I), the oxirane compound represented by formula (II) is added in the presence of the base as occasion demands, to a solution prepared by dissolving the azole compound represented by formula (III) into the diluent, or conversely, an alkali metal salt of the azole compound is added to a solution prepared by dissolving the oxirane compound in the diluent, to react the two compounds. The reaction temperature may be selected optionally in the range of from the solidifying point to the boiling point of the diluent. Practically, however, it is preferable to carry out the reaction at a temperature of from 0° to 120° C., more preferably from 60° to 120° C., for from one to 24 hours under agitation.

After termination of the reaction, the thus obtained reaction mixture is cooled and extracted by an organic solvent such as ethyl acetate, chloroform, methylene chloride, benzene, etc. in iced water. After the organic layer had been separated, washed with water, and dried, the solvent is distilled off under reduced pressure from the organic layer. The thus-obtained residue was purified to obtain the objective compound. The purification procedure can be carried out by subjecting the residue to recrystallization, silica gelchromatography, etc.

The compounds of formula (I) and the physicochemical properties thereof are shown in Table 1. "A type" and "B type" in Table 1 represent the following two types.

⁞⁞⁞ = backward from the plane
— = on the plane
▶ = forward from the plane

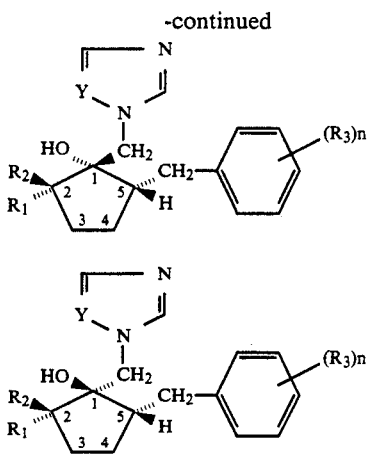

TABLE 1
Azole Derivatives

| Comp. No | Type | R₁ | R₂ | R₃ | n | Y | mp (°C.) |
|---|---|---|---|---|---|---|---|
| 1 | I-A | H | H | 4-F | 1 | N | 135–136 |
| 2 | I-A | H | H | 4-F | 1 | CH | 139–140 |
| 3 | I-A | H | H | 4-Cl | 1 | N | 115–116 |
| 4 | I-A | H | H | 4-Cl | 1 | CH | 115–116 |
| 5 | I-A | H | H | 4-CN | 1 | N | 115–116 |
| 6 | I-A | H | H | 4-CN | 1 | CH | 103–104 |
| 7 | I-A | CH₃ | CH₃ | 2-phenyl | 1 | CH | 132–134 |
| 8 | I-A | CH₃ | CH₃ | 4-phenyl | 1 | CH | 162–163 |
| 9 | I-A | H | H | 2,4-F₂ | 2 | N | 118–119 |
| 10 | I-A | H | H | 2,4-F₂ | 2 | CH | 144–145 |
| 11 | I-A | CH₃ | CH₃ | 4-C(CH₃)₃ | 1 | N | 107–108 |
| 12 | I-A | CH₃ | CH₃ | 4-C(CH₃)₃ | 1 | CH | 167–168 |
| 13 | I-A | CH₃ | CH₃ | 4-C(CH₃)₂H | 1 | N | 46–50 |
| 14 | I-A | CH₃ | CH₃ | 4-C(CH₃)₂H | 1 | CH | 173–177 |
| 15 | I-A | CH₃ | CH₃ | 4-Cl | 1 | N | 113–114 |
| 16 | I-A | CH₃ | CH₃ | 4-Cl | 1 | CH | 133–134 |
| 17 | I-A | CH₃ | CH₃ | 2,4-F₂ | 2 | CH | 127–131 |
| 18 | I-A | CH₃ | CH₃ | 4-CF₃ | 1 | N | 87–92 |
| 19 | I-A | CH₃ | CH₃ | 4-CF₃ | 1 | CH | 124–129 |
| 20 | I-A | H | H | 4-C(CH₃)₂H | 1 | N | 96–100 |
| 21 | I-A | H | H | 4-C(CH₃)₂H | 1 | CH | 124–126 |

The aromatase inhibitory activity was measured in the manner described by Covey, D. F., Biochem. and Biophys. Res. Commun., 157 (1) 81–86 (1988). The inhibitory activity of the aromatase with the compounds was evaluated in a 50% inhibitory concentration (IC$_{50}$) of the aromatase activity. The IC$_{50}$ was less than $2 \times 10^{-5}$M.

The compounds of formula (I) have inhibitory activity for the aromatase, so they are useful as aromatase inhibitors and useful for treating estrogen-dependent diseases such as breast cancer, prostatic cancer, ovarian cancer, uterine tumor, pancreatic carcinoma, endometriosis, polycystic ovarian disease, benign breast disease, and Cusing's syndrome carcinoma.

The acute toxicity (LD$_{50}$) of the compounds in mice is greater than 500 mg/kg; therefore, the compounds are clinically safe.

The compounds of formula (I) may be administered by various routes such as the oral, subcutaneous, intramuscular, intravenous, transdermal, and rectal routes.

The compounds of formula (I) are usually employed in the form of pharmaceutical compositions. Such compositions comprise, as active ingredient, the compounds and a pharmaceutically acceptable carrier. Usually the compound is mixed with a carrier, or diluted by a carrier, or enclosed with a carrier which may be in the form of a capsule or a container.

When the carrier is a diluent, it may be a solid, semisolid, or liquid material which acts as a vehicle, excipient, or medium. Thus, the compositions may be in the form of tablets, pills, powders, elixirs, emulsions, solutions, syrups, suspensions, aerosols, ointments, soft and hard gelatin capsules, suppositories, sterile injectable solutions, and sterile packaged powders.

Some examples of suitable carriers and diluents include lactose, dextrose, sucrose, sorbitol, mannitol, starch, calcium phosphate, calcium silicate, microcrystalline cellulose, polyvinylpyrrolidone, cellulose, gelatin, syrup, methylcellulose, polyoxyethylene sorbitan mono-oleate, methyl- and propylhydroxybenzoates, talc, magnesium stearate, and water.

The formulations constituting compositions used in the present invention can additionally include lubricating agents, wetting agents, emulsifying and suspending agents, preserving agents, sweetening agents, or flavoring agents. For oral administration, the compounds of this invention can be admixed with carriers or diluents and molded into tablets or enclosed in gelatin capsules. The mixtures can alternatively be dissolved in liquids such as an aqueous solution, isotonic saline, sterile water, or the like, and administered intravenously or by injection.

The compositions are preferably formulated in a unit dosage form, each dosage containing from about 0.01 to about 500 mg, preferably about 0.1 to about 300 mg, of the active ingredient.

The compounds of formula (I) are effective over a wide dosage range. For example, dosages per day will normally fall within the range of about 0.005 to about 100 mg/kg of body weight.

In the treatment of adult humans, a range of about 0.01 to about 40 mg/kg, in single or divided doses, is preferred. However, it will be understood that the amount of the compounds actively administered will be determined by a physician, in the light of the relevant circumstances including the condition to be treated, the age of the patient, the severity of the patient's symptoms, and the route of administration. Therefore, the above dosage ranges are not intended to limit the scope of the invention in any way.

The following examples are representative of the invention.

EXAMPLE 1

Preparation of methyl 1-(p-Fluoro benzyl)-2-oxocyclopentanecarboxylate

To a stirred suspension of n-hexane-washed sodium hydride (0.94 g, 39.0 mmol, 1.3 eq) there was added a solution of ethoxyethyl 2-oxocyclopentane-carboxylate (4.26 g, 30.0 mmol, 1.0 eq) in DMF (15 ml) at 0° C. The resulting solution was warmed to room temperature and then stirred for 30 min: the solution became orange. After terminal evolution of hydrogen had been confirmed, p-fluorobenzyl bromide (6.80 g, 36.0 m mol, 1.2 eq) was added to the resulting solution at 0° C. The reaction mixture was then warmed to room temperature and stirred overnight.

After terminal reaction had been confirmed by TLC, the resulting solution was poured onto ice-cold water and extracted with ethyl acetate. The organic layer was washed with brine, dried over anhydrous sodium sulfate, and concentrated under reduced pressure. A crude product (9.82 g) was obtained. The crude product was purified by SiO₂ column chromatography eluting with n-hexane/ethyl acetate (4:1) to give the title compound as a white crystal (6.61 g, 88.3%; mp 58°-60° C.).

EXAMPLE 2

Preparation of 2-(p-Fluorobenzyl)cyclopentanone

To a stirred solution of glacial acetic acid (100 ml) and an aqueous solution of sulfuric acid (12.5% 50 ml), there was added methyl 1-(p-fluorobenzyl)-2 -opentanecarboxylate (14.46 g, 57.8 mmol). The mixture was refluxed under argon for 4 h.

After the product had been confirmed by TLC, the resulting solution was poured onto ice-cold water (50 ml) and extracted with diethyl ether (200 ml×2). The organic layers were washed with brine, dried over anhydrous sodium sulfate, and concentrated under reduced pressure to give a crude product (12.67 g).

The crude product was purified by SiO₂ column chromatography eluting with n-hexane/ethyl acetate (6:1) to give the title compound as a yellowish liquid (Rf 0.47 n-hexane/ethyl acetate (2:1)).

EXAMPLE 3

Preparation of 4-(p-Fluorobenzyl)-1-oxaspiro [2.4]heptane

Trimethylsulfoxonium iodide (6.6 g, 30.1 mmol, 1.3 eq) was dissolved in DMSO (35 ml) at room temperature and sodium hydride (0.67 g, 27.8 mmol, 1.2 eq) was added at 10° C. while being stirred to form a solution.

After the solution had been heated at room temperature and stirred for 30 min, the resulting solution became yellowish transparent. Upon confirmation of the terminal evolution of hydrogen, the solution was again warmed to 10° C. and 2- (p-fluorobenzyl) cyclopentanone (4.45 g, 23.2 mmol, 1.0 eq) was dripped into the solution. Then, the solution was stirred at room temperature for 3 h, poured onto ice cold water (30 ml), and extracted with diethyl ether (100 ml×2).

The organic layers were washed with brine, dried over anhydrous sodium sulfate, and concentrated under reduced pressure to give a crude product as a yellowish liquid (4.01 g, 83.9%; Rf 0.55 n-hexane/ethyl acetate (2:1)).

EXAMPLE 4

Preparation of 2-(p-Fluorobenzyl)-1-(1,2,4-triazoly-1-yl-methyl)cyclopentanol (Comp. No. 1)

4-(p-fluorobenzyl)-1-oxaspiro[2.4]heptane (0.66 g, 3.2 mmol, 1.0 eq) was dissolved in DMF (10 ml). There was then added sodium 1,2,4-triazole (0.38 g, 4.2 mmol, 1.3 eq) and the solution was stirred at 70° C. under argon overnight. The resulting solution was poured onto ice-cold water and then extracted with ethyl acetate.

The organic layer was washed with a saturated aqueous solution of sodium chloride, dried over anhydrous sodium sulfate, and concentrated under reduced pressure to give a crude product (0.93 g). The crude product was recrystallized from n-hexane/ethyl acetate to give the title compound as a white crystal (Comp. No. 1; mp 135°-136° C.; 0.70 g, 79.5%).

EXAMPLE 5

Preparation of2-(-Fluorobenzyl)-1-(imidazoly-1-ylmethyl)cyclopentanol (Comp. No. 2)

4-(p-fluorobenzyl)-1-oxaspiro[2.4]heptane (0.67 g, 3.3 mmol, 1.0 eq) was dissolved in DMF (10 ml), and sodium imidazole (0.38 g, 4.2 mmol, 1.3 eq) was added to the mixture. Stirring at 70 C in a stream of argon was carried out overnight. The resulting solution was poured onto ice-cold water and extracted with ethyl acetate.

The organic layer was washed with brine, dried over anhydrous sodium sulfate, and concentrated under reduced pressure to give a crude product (0.93 g). The crude product was recrystallized from n-hexane/ethyl acetate to give the title compound as a white crystal (Comp. No. 2; mp 139°-140° C.; 0.80 g, 93.0%).

EXAMPLE 6

Preparation of Methyl 1-(2,4-difluorobenzyl)-2-oxocyclopentanecarboxylate

To a stirred suspension of n-hexane-washed sodium hydride (0.58 g, 24 mmol, 1.2 eq), there was added a solution of methyl 2-oxocyclopentanecarboxylate (2.84 g, 20.0 mmol, 1.0 eq) in DMF (20 ml) at 10° C. After the suspension had been heated at room temperature and then stirred for 30 min, the suspension became yellowish. Upon confirmation of the terminal evolution of hydrogen, the resulting solution was again warmed to 10° C. and 2,4-difluorobenzyl bromide (5.38 g, 26.0 mmol, 1.3 eq) was added. The solution was warmed to room temperature and stirred for 2 h. After the terminal reaction had been confirmed by TLC, the resulting solution was poured onto ice-cold water (30 ml) and washed with diethyl ether (100 ml×2).

The organic layers were washed with brine, dried over anhydrous sodium sulfate, and concentrated under reduced pressure to give a crude product (6.03 g). The crude product was purified by chromatography on a column eluting with n-hexane/ethyl acetate (4:1) to give the title compound as a white crystal (5.14 g, 95.8%; mp 55°-58° C.).

EXAMPLE 7

Preparation of 2-(2,4-Difluorobenzyl) cyclopentanone

To a stirred solution of glacial acetic acid (100 ml) and an aqueous solution of sulfuric acid (12.5%, 30 ml), there was added methyl 1-(2,4-difluorobenzyl)-2-oxocyclopentanecarboxylate (5.14 g, 21.6 mmol). The mixture was refluxed in a stream of argon for 5 h.

After the product had been confirmed by TLC, the resulting solution was poured onto ice-cold water (50 ml) and extracted with diethyl ether (200 ml×2). The organic layers were washed with brine, dried over anhydrous sodium sulfate, and concentrated under reduced pressure to give a crude product (4.07 g).

The crude product was purified by chromatography on a column eluting with n-hexane/ethyl acetate (4:1) to give the title compound as a yellowish liquid (3.579 g, 78.7%. Rf 0.52 n-hexane/ethyl acetate (2:1)).

EXAMPLE 8

Preparation of 4-(2,4-Difluorobenzyl)-1-oxaspiro[2.4]heptane

Trimethylsulfoxonium iodide (4.86 g, 22.1 mmol, 1.3 eq) was dissolved in DMSO (25 ml) and sodium hydride (0.49 g, 20.4 mmol, 1.2 eq) was added at 100° C. while being stirred. The solution was warmed to room temperature and stirred for 45 min while being stirred; thereafter, the solution became transparent. After terminal evolution of hydrogen had been confirmed, the solution was again heated at 10° C. and 2-(2,4-difluorobenzyl)cyclopentanone (3.56 g, 17.0 mmol, 1.0 eq) was dripped into the solution.

The solution was stirred at room temperature for 3 h, then poured onto ice-cold water, and extracted with diethyl ether (80 ml×2).

The organic layers were washed with brine, dried over anhydrous sodium sulfate, and concentrated to give a crude product as a yellowish liquid (3.35 g, 37.9%; Rf 0.55 n-hexane/ethyl acetate (2:1)).

EXAMPLE 9

Preparation of 2-(2,4-Difluorobenzyl)-1-(1,2,4-triazoly-1-yl-methyl)cyclopentanol (Comp. No. 9)

4-(2,4-Difluorobenzyl)-1-oxaspiro[2.4]heptane (1.67 g, 7.5 mmol, 1.0 eq) was dissolved in DMF (10 ml) and sodium 1,2,4-triazole (0.88 g, 9.7 mmol, 1.3 eq) was added to the mixture. Stirring at 70° C. under argon was carried out overnight. The resulting solution was poured onto ice-cold water (1o ml) and extracted with ethyl acetate (50ml×2).

The organic layers were washed with brine, dried over anhydrous sodium sulfate, and concentrated under reduced pressure to give a crude product (2.79 g).

The crude product was recrystallized from n-hexane/ethyl acetate to give the title compound as a white crystal (Comp. No. 9; mp 118°-119° C.; 0.46 g, 18.3%).

EXAMPLE 10

Preparation of 2-(2,4-Difluorobenzyl)-1-(imidazoly-1-yl-methyl)cyclopentanol (Comp. No. 10)

4 (2,4-Difluorobenzyl)-1-oxaspiro[2.4]heptane (1.67 g, 7.5 mmol, 1.0 eq) was dissolved in DMF (10 ml). Sodium imidazole (0.87 g. 9.7 mmol, 1.3 eq) was added to the solution. Stirring at 70 C under argon was carried out overnight. The resulting solution was poured onto ice-cold water and extracted with ethyl acetate (50 ml×2).

The organic layers were washed with brine, dried over anhydrous sodium sulfate, and concentrated to give a crude product (3.04 g). The crude product was recrystallized from n-hexane/ethyl acetate to give the title compound as a white crystal (Comp. No. 10; mp 144°-145° C.; 0.618, 28.0%).

The compounds of formula (1) in Table 1 were obtained by the same procedure as in the above examples.

EXAMPLE 11

Aromatase activity was measured in the manner described by Covey, D. F., Biochem. Biophys. Res. Commun. 157 (1), 81-86 (1988).

The inhibitory activity of the aromatase with the compounds was evaluated in 50% inhibitory concentration ($IC_{50}$) of the aromatase.

An aromatase base was taken from microsomes of human placenta and [19-$^{14}$C]4-androstene-3,17 dione was used as a substrate. $H^{14}COOH$ was released into a reaction mixture after aromatization and its radioactivity was measured to evaluate the aromatase activity.

The inhibitory activity of the aromatase and the concentration of the compounds were depicted in a graph from which the $IC_{50}$ was calculated.

To a solution of phosphoric acid buffer, [19-$^{14}$C]4-androstene-3,17-dione ($1 \times 10^{-6}$M, 2 kBq/ml), microsomes arising from human placenta (0.1 mg/ml, protein concentration), coenzyme ($2 \times 10^{-3}$M, NADH), glucose-6-phosphoric acid ($4 \times 10^{-3}$M), and glucose-6-phosphoric acid dehydrogenase (4U/ml) were added and reacted under stirring at 37° C. for 30 min.

The compound that was dissolved in DMSO was added into the reaction mixture and the final concentration of MDSO was in the range of 0.1 to 0.55% by volume. Chloroform (5 ml) was then added into the reaction mixture to terminate the reaction and to allow for recovery of the $H^{14}COOH$ in a water layer. The collected water layer (0.1 ml) was added in liquid scintillation cocktail (Atomlight, duPont, 4 ml) to measure its radioactivity. 4-Hydroxyandrostenedione was used as a positive control. The results are shown in Table 2.

TABLE 2

| Comp. No. | $IC_{50}$ (M) |
| --- | --- |
| 1 | $3.5 \times 10^{-6}$ |
| 2 | $7.0 \times 10^{-6}$ |
| 3 | $3.8 \times 10^{-6}$ |
| 4 | $5.0 \times 10^{-6}$ |
| 5 | $7.3 \times 10^{-6}$ |
| 6 | $4.5 \times 10^{-6}$ |
| 7 | $3.7 \times 10^{-6}$ |
| 8 | $4.1 \times 10^{-6}$ |
| 9 | $7.5 \times 10^{-6}$ |
| 10 | $4.8 \times 10^{-7}$ |
| 11 | $2.6 \times 10^{-6}$ |
| 12 | $4.2 \times 10^{-6}$ |
| 13 | $8.4 \times 10^{-6}$ |
| 14 | $6.0 \times 10^{-6}$ |
| 15 | $4.7 \times 10^{-6}$ |
| 16 | $3.0 \times 10^{-7}$ |
| 17 | $4.0 \times 10^{-7}$ |
| 18 | $7.2 \times 10^{-6}$ |
| 19 | $5.5 \times 10^{-6}$ |
| 20 | $4.3 \times 10^{-6}$ |
| 21 | $6.3 \times 10^{-6}$ |
| Control | $2.0 \times 10^{-5}$ |

EXAMPLE 12

Female Sprague-Dawley rates aged 50 days were orally given 7,12-dimethylbenzanthracene (15 mg/kg) and observed for two months. The rats that developed spontaneous mastocarcinoma were selected and divided into three groups of 15 animals.

The first group was administered daily an ip injection for 20 consecutive days in an amount of 20 mg/kg (body weight) of the compounds in a physiological salt solution (10 ml).

The second group was also treated in the same manner as the first group except that 4-hydroxyandrostenedione was used as a positive control.

The third group was administered only an amount of 10 ml of a physiological salt solution.

After 5 days from the last injection, the rats were sacrificed to enucleate tumors.

The tumors were weighed and the mean tumor weight (T) of the first and the second groups was calculated. The mean tumor weight (C) of the third group was also calculated. On the basis of these results, the inhibition rate of tumor growth was calculated from the following equation.

$$\text{Inhibition rate (I.R.) (\%)} = \frac{C - T}{C} \times 100$$

The results are shown in Table 3.

TABLE 3

| Comp. No. | I.R. (%) |
|---|---|
| 1 | 60 |
| 2 | 70 |
| 3 | 64 |
| 4 | 74 |
| 5 | 60 |
| 6 | 53 |
| 7 | 58 |
| 8 | 60 |
| 9 | 72 |
| 10 | 85 |
| 11 | 71 |
| 12 | 73 |
| 13 | 55 |
| 14 | 63 |
| 15 | 74 |
| 16 | 83 |
| 17 | 67 |
| 18 | 65 |
| 19 | 63 |
| 20 | 60 |
| 21 | 72 |
| Control | 48 |

EXAMPLE 13

This formulation relates to one example of a pharmaceutical composition. The pharmaceutical composition as made of the following ingredients in the indicated amounts.

| | |
|---|---|
| Compound No. 1 | 100 mg |
| Polyoxyethylene Sorbitan Mono-oleate | 50 mg |
| Starch | 250 mg |

The composition was mixed uniformly to give a powder and put into a capsule.

What is claimed is:

1. A method of inhibiting aromatase in a patient comprising administering to the patient in need thereof an aromatase-inhibiting amount of a compound of the formula

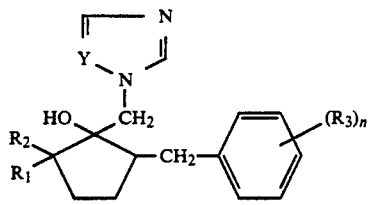

wherein
- $R_1$ represents hydrogen atom or ($C_1$-$C_5$) alkyl;
- $R_2$ represents hydrogen atom or ($C_1$-$C_5$) alkyl;
- $R_3$ represents halogen atom, ($C_1$-$C_5$) alkyl, trifluoromethyl, phenyl, or cyano, $R_3$ being either the same or different;
- n represents an integer of 1 or 2; and
- Y represents nitrogen atom or CH; or a pharmaceutically acceptable salt thereof.

2. The method of claim 1 wherein said compound is of the formula

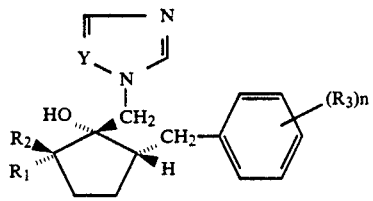

wherein $R_1$, $R_2$, $R_3$, Y, and n have the same meaning as in claim 1.

3. A method of treating estrogen-dependent diseases by inhibiting aromatase in a patient comprising administering to a patient in need thereof an effective amount of a compound of the formula

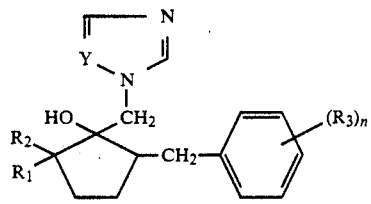

wherein
- $R_1$ represents hydrogen atom or ($C_1$-$C_5$) alkyl;
- $R_2$ represents hydrogen atom or ($C_1$-$C_5$) alkyl;
- $R_3$ represents halogen atom, ($C_1$-$C_5$) alkyl, trifluoromethyl, phenyl, or cyano, $R_3$ being either the same or different; and
- Y represents a nitrogen atom or CH; and
- n represents an integer of 1 or 2; or a pharmaceutically acceptable salt thereof.

4. The method of claim 3 wherein the compound is of the formula:

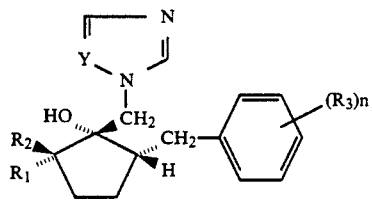

wherein $R_1$, $R_2$, $R_3$, Y, and n have the same meaning as in claim 3.

* * * * *

UNITED STATES PATENT AND TRADEMARK OFFICE
CERTIFICATE OF CORRECTION

PATENT NO. : 5,286,737  Page 1 of 3
DATED : February 15, 1994
INVENTOR(S) : Kato et al.

It is certified that error appears in the above-indentified patent and that said Letters Patent is hereby corrected as shown below:

On the title page, [57] ABSTRACT, line 1 after the formula, change "a is" to --is a--.

Column 2, line 32, change "oxocyclopentanecarboxy" to --oxocyclopentanecarboxylic--;

Column 6, line 15, change "propylhydroxybenzoates" to --propyl-hydroxybenzoates--;

line 51, change "Fluoro" to --Fluoro- --; and line 54, before "there" insert a comma --,--.

Column 7, line 11, change "-open-" to -- -oxocyclopen- --;

line 52, change "(1,2,4-triazoly-1-yl-methyl)" to --(1,2,4-triazol-1-ylmethyl)--; and line 55, change "(p-fluorobenzyl) to --(p-Fluorobenzyl)--.

UNITED STATES PATENT AND TRADEMARK OFFICE
CERTIFICATE OF CORRECTION

PATENT NO. : 5,286,737

DATED : February 15, 1994

INVENTOR(S) : Kato, et al

It is certified that error appears in the above-indentified patent and that said Letters Patent is hereby corrected as shown below:

Column 8, line 4, change "of2-(-Fluorobenzyl)-1-(imidazoly-1" to --of 2-(p-Fluorobenzyl)-1-(imidazol-1 --;

line 7, change "(p-fluorobenzyl) to --(p-Fluorobenzyl)--; and line 24, change "(2,4-difluorobenzyl) to --(2,4-Difluorobenzyl).

Column 9, line 26, change "(1,2,4-triazoly-1-yl-methyl)" to --(1,2,4-triazol-1-ylmethyl)--;

line 34, change "1o" to --10--;

line 46, change "of2" to --of 2-- and change "(imidazoly-1-yl-methyl)" to --(imidazol-1-ylmethyl)--;

line 49, change "4 (2," to --4-(2,--; and line 51, change "70C" to --70°C--.

UNITED STATES PATENT AND TRADEMARK OFFICE
CERTIFICATE OF CORRECTION

PATENT NO. : 5,286,737

DATED : February 15, 1994

INVENTOR(S) :

It is certified that error appears in the above-indentified patent and that said Letters Patent is hereby corrected as shown below:

Column 10, line 5, change "17 dione" to --17-dione--;

line 21, change "MDSO" to --DMSO--; and line 55, change "rates" to --rats--.

Signed and Sealed this

Eighteenth Day of October, 1994

Attest:

BRUCE LEHMAN

*Attesting Officer*   *Commissioner of Patents and Trademarks*